(12) United States Patent
Sano et al.

(10) Patent No.: US 9,986,920 B2
(45) Date of Patent: Jun. 5, 2018

(54) BLOOD PRESSURE INFORMATION MEASUREMENT DEVICE CUFF AND BLOOD PRESSURE INFORMATION MEASUREMENT DEVICE PROVIDED THEREWITH

(75) Inventors: Yoshihiko Sano, Kyoto (JP); Hideaki Yoshida, Kyoto (JP); Minoru Taniguchi, Kyoto (JP)

(73) Assignee: OMRON HEALTHCARE Co., Ltd., Kyoto (JP)

(*) Notice: Subject to any disclaimer, the term of this patent is extended or adjusted under 35 U.S.C. 154(b) by 1248 days.

(21) Appl. No.: 13/538,371

(22) Filed: Jun. 29, 2012

(65) Prior Publication Data

US 2012/0330169 A1 Dec. 27, 2012

Related U.S. Application Data

(63) Continuation of application No. PCT/JP2010/072652, filed on Dec. 16, 2010.

(30) Foreign Application Priority Data

Dec. 29, 2009 (JP) ................. 2009-299152

(51) Int. Cl.
  *A61B 5/02* (2006.01)
  *A61B 5/022* (2006.01)
  *A61B 5/021* (2006.01)
(52) U.S. Cl.
  CPC ...... *A61B 5/02233* (2013.01); *A61B 5/02141* (2013.01)
(58) Field of Classification Search
  CPC .. A61B 5/02141; A61B 5/02233; A61B 5/022
  See application file for complete search history.

(56) References Cited

U.S. PATENT DOCUMENTS 6,228,035 B1 * 5/2001 Packman ........... A61B 5/02141
                                                128/900
6,379,310 B1    4/2002 Mori et al.
(Continued)

FOREIGN PATENT DOCUMENTS

CN      101346100 A       1/2009
EP        1125546 A1 *   8/2001  ......... A61B 5/02125
(Continued)

OTHER PUBLICATIONS

Office Action issued in corresponding Japanese Application No. 2009-299152 dated Sep. 10, 2013, and English translation thereof (4 pages).
(Continued)

*Primary Examiner* — Jacqueline Cheng
*Assistant Examiner* — Eric Messersmith
(74) *Attorney, Agent, or Firm* — Osha Liang LLP

(57) ABSTRACT

In a blood pressure information measurement device cuff, a first flexion point and a second flexion point at which a curvature radius changes are provided in a curler, and a straight line-shaped connection portion is provided between the first flexion point and the second flexion point so as to be located inside a curve formed by extending a first curved portion and a second curved portion that are located at the ends of the curler at the first flexion point and the second flexion point, according to the respective curvatures. Through this, it is possible to provide a blood pressure information measurement device cuff, and a blood pressure information measurement device provided with such a cuff, that can reduce error in a blood pressure measurement by reducing errors in changes in the volume of a fluid bladder.

4 Claims, 10 Drawing Sheets

(56) References Cited

U.S. PATENT DOCUMENTS

| | | | |
|---|---|---|---|
| 6,645,157 B2 * | 11/2003 | Inagaki | A61B 5/02233 600/485 |
| 2006/0058687 A1 | 3/2006 | Kishimoto et al. | |
| 2009/0234381 A1 | 9/2009 | Karo | |

FOREIGN PATENT DOCUMENTS

| | | |
|---|---|---|
| JP | 02-001221 A | 1/1990 |
| JP | 06038931 A | 2/1994 |
| JP | 11197123 A | 7/1999 |
| JP | 2006-081655 A | 3/2006 |
| TW | 200803787 A | 1/2008 |
| WO | 99/35962 A1 | 7/1999 |
| WO | 2007/074589 A1 | 7/2007 |
| WO | 2007/119482 A1 | 10/2007 |

OTHER PUBLICATIONS

Office Action issued in corresponding Chinese Application No. 201080059928.7 dated Mar. 5, 2014 (10 pages).
International Search Report issued in PCT/JP2010/072652 dated Jan. 18, 2011 (1 page).
espacenet, Patent Abstract for Japanese Publication No. 06-038931, published Feb. 15, 1994 (1 page).
espacenet, Patent Abstract for Japanese Publication No. 02-001221, published Jan. 5, 1990 (1 page).
espacenet, Patent Abstract for Japanese Publication No. 2006-081655, published Mar. 30, 2006 (1 page).
espacenet, Patent Abstract for Japanese Publication No. 11-197123, published Jul. 27, 1999 (1 page).

* cited by examiner

BLOOD PRESSURE INFORMATION MEASUREMENT DEVICE CUFF AND BLOOD PRESSURE INFORMATION MEASUREMENT DEVICE PROVIDED THEREWITH

This is a continuation of application Serial No. PCT/JP2010/072652 filed Dec. 16, 2010, the contents of which are incorporated herein by reference.

BACKGROUND OF THE INVENTION

Field of the Invention

The present invention relates to blood pressure information measurement device cuffs that are used while being worn on a measurement area when measuring blood pressure information such as a blood pressure value, and to blood pressure information measurement devices provided with such cuffs.

Description of the Background Art

Blood pressure information measurement devices obtain blood pressure information of a measurement subject. The blood pressure information obtained by such blood pressure information measurement devices includes various types of information related to the circulatory system, such as a systolic blood pressure value (a maximum blood pressure value), a diastolic blood pressure value (a minimum blood pressure value), an average blood pressure value, a sphygmogram, pulse, AI (Augmentation Index) value, and the like of the measurement subject, and so on. Stress on the heart, changes in the hardness of arteries, or the like can be understood based on this blood pressure information. A blood pressure information measurement device is used in the early discovery, prevention, treatment, and so on of circulatory system conditions.

Generally speaking, a blood pressure information measurement device cuff (called simply a "cuff" hereinafter) is used in the measurement of blood pressure information. Such a cuff has a bladder-shaped cover member, formed having a band shape, that has an internal cavity, and a fluid bladder for applying pressure to a body (an artery) is contained within the bladder-shaped cover member. The cuff is wrapped around a part of the body, such as the upper arm.

In a blood pressure information measurement device used to measure blood pressure values such as a systolic blood pressure value or a diastolic blood pressure value (called simply a "sphygmomanometer" hereinafter), the cuff is wrapped around the surface of part of the body. A fluid such as air, a liquid, or the like is injected into or exhausted from the fluid bladder enclosed within the cuff. The fluid bladder is inflated by injecting a fluid into the fluid bladder. On the other hand, the fluid bladder is deflated by exhausting the fluid from the fluid bladder. Changes in the pressure within the fluid bladder produced when the fluid bladder inflates or deflates are registered as an arterial sphygmogram or a blood pressure value.

Generally speaking, measuring blood pressure through a non-invasive blood pressure measurement method involves wrapping the cuff around the upper arm, increasing the air pressure within the cuff in order to stop the flow of blood, and pressurizing the artery. At this time, it is extremely important to adjust the tightness caused by friction produced between the air bladder and other internal components such as the bladder-shaped cover member, ensure that the tightness of the cuff does not decrease during measurement, and align the center position of the air bladder directly above the artery.

There are devices that include a curler, configured of an approximately cylindrical, flexible member that guides the cuff along the upper arm, in order to facilitate the tightening of the cuff so as to follow the upper arm. JP-H2-1221A (Patent Literature 1) and JP-H6-38931A (Patent Literature 2) can be given as disclosures of such a cuff.

When pressure is applied to the upper arm using an air bladder, if, for example, the air bladder is inflated in an approximately cylindrical shape while wrapped loosely upon the measurement subject, there are cases where the volume of the air within the cuff will become more than ten times greater the volume within the blood vessels. In such a case, the measured blood pressure value will be a measurement result that contains more error than a normal blood pressure measurement value.

FIG. 13 is a schematic diagram illustrating a cross-section of an upper arm 301. The upper arm 301 contains a bone 302, and an artery 303 is located at a position closer to the subject's body from a top position (L2) of the upper arm 301. FIG. 14 is a cross-sectional schematic diagram illustrating a state in which a cuff has been properly affixed to the upper arm. The center position of an air bladder 361 is positioned directly above the artery 303, and the air bladder 361 is suitably biased toward a measurement area by a curler 391. Note that in FIG. 14, a bladder-shaped cover member configured as a band, which houses the air bladder 361 and the curler 391, is not shown. The same applies to FIG. 15.

FIG. 15 is a cross-sectional schematic diagram illustrating a state in which the cuff has been wrapped around the upper arm loosely. Although the center position of the air bladder 361 is located directly above the artery 303, there is a large distance between the curler 391 and the upper arm 301 (that is, a distance R2 is longer than a distance R1 shown in FIG. 14), which causes an increase in the volume of the air bladder 361 (that is, an expansion of the air volume within the cuff), resulting in a state where the artery 303 cannot be sufficiently pressurized. As a result, the measured blood pressure value will be a measurement result that contains more error than a normal blood pressure measurement value.

SUMMARY OF THE INVENTION

The problem this invention is to solve is that a blood pressure value measured by a blood pressure information measurement device will be a measurement result that contains more error than a normal blood pressure measurement value in the case where a blood pressure information measurement device cuff has been wrapped around a measurement area loosely. It is thus an object of this invention to provide a blood pressure information measurement device cuff, and a blood pressure information measurement device provided with such a cuff, that can reduce error in a blood pressure measurement by reducing errors in changes in the volume of a fluid bladder, even in the case where the blood pressure information measurement device cuff has been wrapped around a measurement area loosely.

A blood pressure information measurement device cuff according to one aspect of the present invention includes: a fluid bladder for applying pressure to a measurement area; a curler for biasing the fluid bladder toward the measurement area; and a bladder-shaped cover member that houses the fluid bladder and the curler and is configured as a band that is wrapped around the measurement area in order to affix the fluid bladder and the curler to the measurement area. The curler is formed in a curved shaped that follows the direction in which the curler is wrapped around the measurement area, and includes a first flexion point and a second flexion point at which the curvature radius of the curler changes; an area between the first flexion point and the second flexion point is formed so as to be further inside from a curve formed by extending the curvature of the curler from the ends of the curler at the first flexion point and the second flexion point; and a center position between the first flexion point and the second flexion point overlaps with a center position of the fluid bladder that follows the direction in which the fluid bladder is wrapped around the measurement area.

A blood pressure information measurement device cuff according to another aspect of the invention includes: a fluid bladder for applying pressure to a measurement area; a curler for biasing the fluid bladder toward the measurement area; and a bladder-shaped cover member that houses the fluid bladder and the curler and is configured as a band that is wrapped around the measurement area in order to affix the fluid bladder and the curler to the measurement area. The curler is formed in a curved shaped that follows the direction in which the curler is wrapped around the measurement area, and includes a first flexion point and a second flexion point at which the curvature radius of the curler changes; an area between the first flexion point and the second flexion point is formed so as to be further inside from a curve formed by extending the curvature of the curler from the ends of the curler at the first flexion point and the second flexion point; and a portion of the curler between the first flexion point and the second flexion point is disposed so as to overlap with a center position of the fluid bladder.

In a blood pressure information measurement device cuff according to another aspect of the invention, the area between the first flexion point and the second flexion point has a region that forms a straight line.

In a blood pressure information measurement device cuff according to another aspect of the invention, the distance between the first flexion point and the second flexion point is approximately 20 mm to approximately 60 mm.

A blood pressure information measurement device according to the present invention includes one of the stated blood pressure information measurement device cuffs, an inflation/deflation mechanism that inflates/deflates the fluid bladder, and a blood pressure information obtainment unit that obtains blood pressure information.

According to the present invention, it is possible to provide a blood pressure information measurement device cuff and a blood pressure information measurement device provided therewith that are capable of taking accurate blood pressure measurements even in the case where the blood pressure information measurement device cuff has been loosely wrapped around a measurement area.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
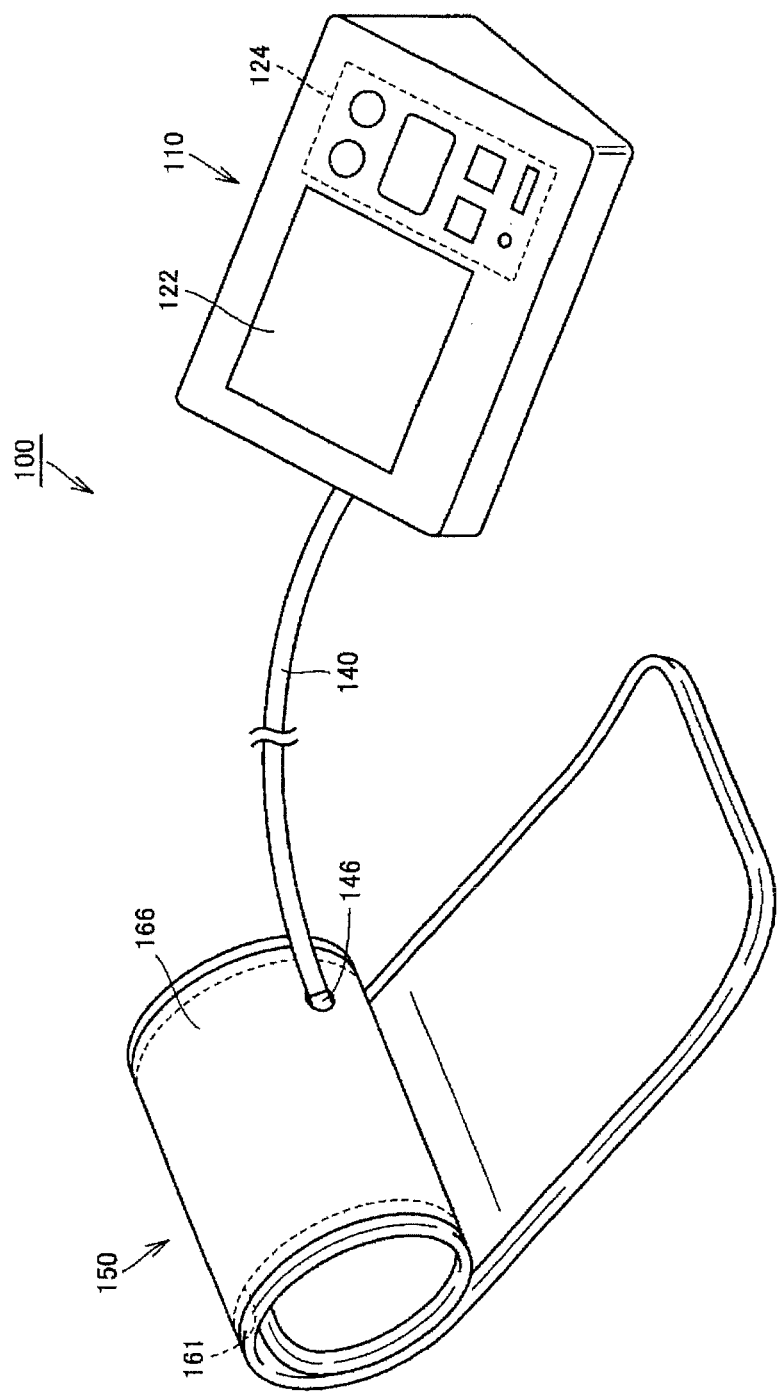
FIG. 1 is a diagram illustrating the overall configuration of a sphygmomanometer according to an embodiment.

A blood pressure information measurement device cuff and a blood pressure information measurement device provided therewith according to an embodiment of the present invention will be described hereinafter with reference to the drawings.

In the following embodiment, a sphygmomanometer cuff that is used by being wrapped around an upper arm will be described as an example of a blood pressure information measurement device cuff. A sphygmomanometer capable of measuring blood pressure values such as a systolic blood pressure value and a diastolic blood pressure value using the sphygmomanometer cuff will be described as an example of the blood pressure information measurement device provided with the blood pressure information measurement device cuff.

When numbers, amounts, and so on are discussed in the following embodiment, it should be noted that unless explicitly mentioned otherwise, the scope of the present invention is not necessarily limited to those numbers, amounts, and so on. In the embodiment described hereinafter, identical and corresponding components may be assigned identical reference numerals, and redundant descriptions thereof may be omitted.

Figure 2:
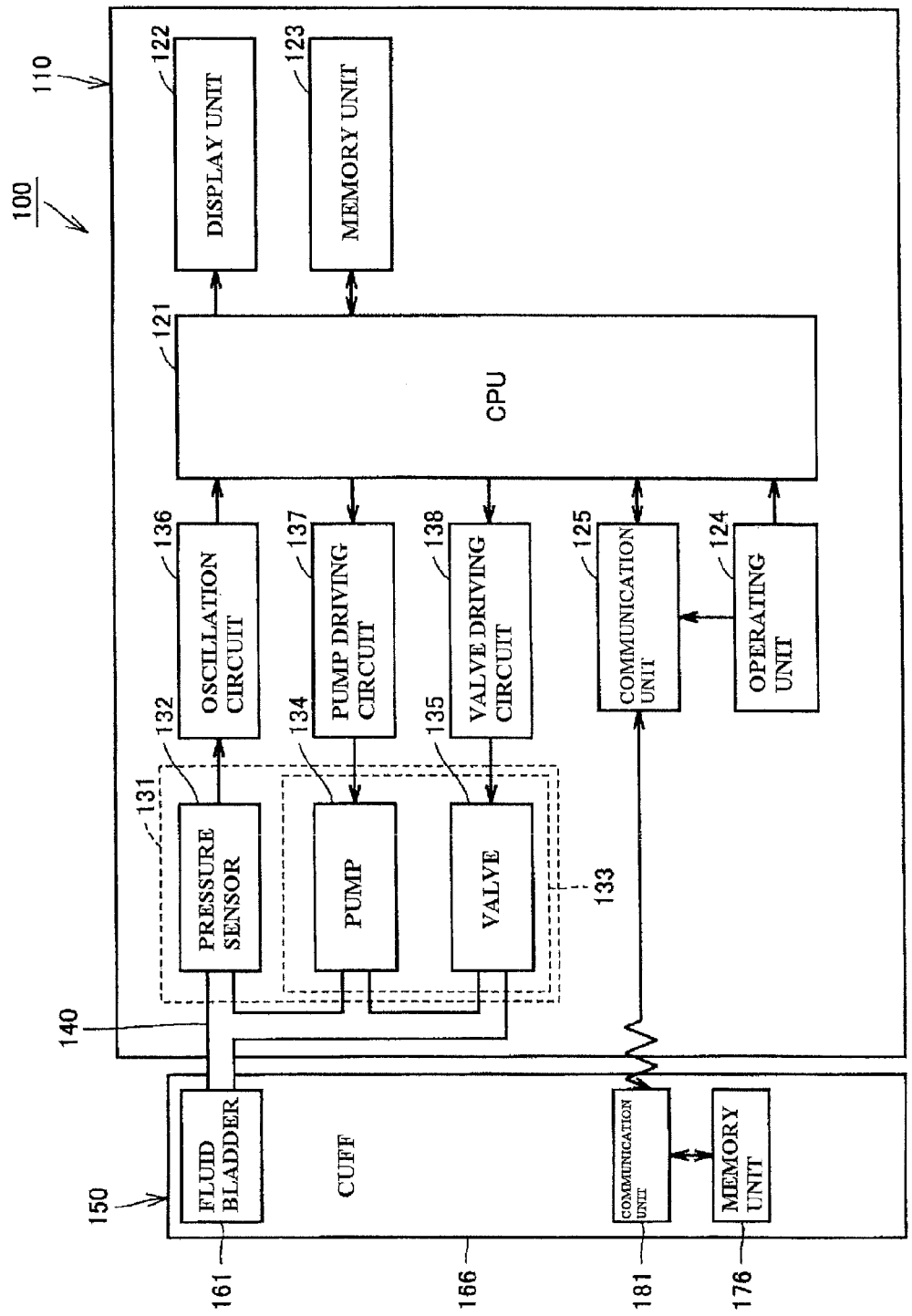
FIG. 2 is a function block diagram illustrating the configuration of the sphygmomanometer according to the embodiment.
Figure 3:
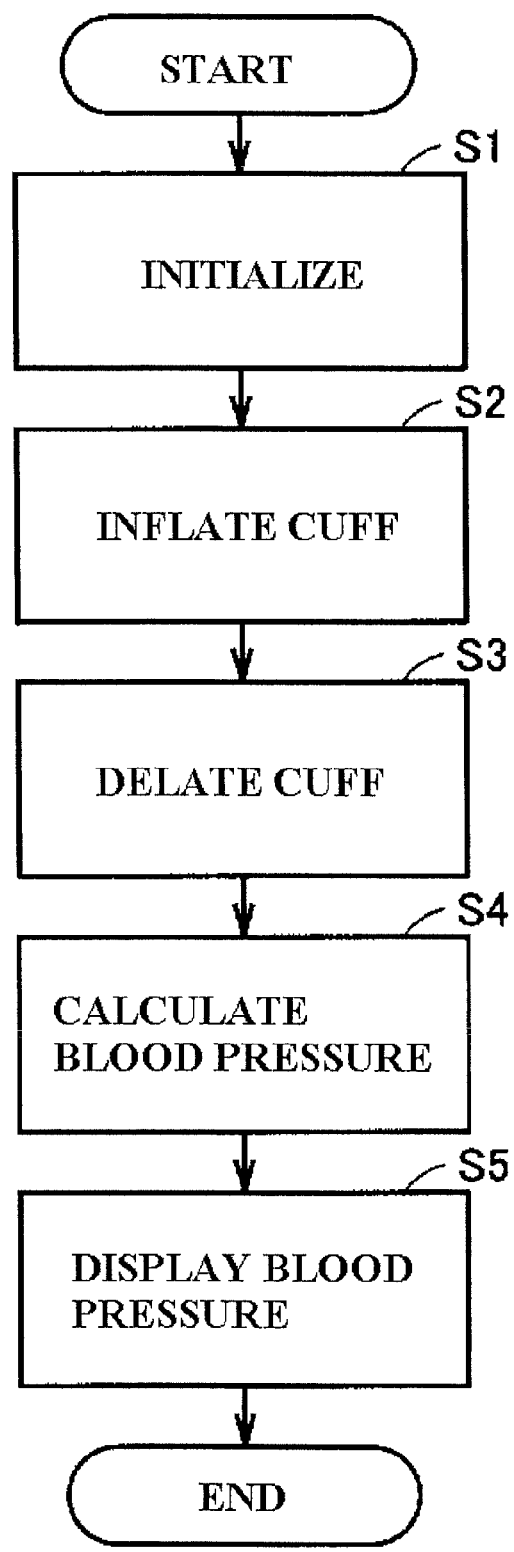
FIG. 3 is a flowchart illustrating the flow of a blood pressure measurement process performed by the sphygmomanometer according to the embodiment.

First, a sphygmomanometer 100 according to the present embodiment will be described with reference to FIGS. 1 through 3. Note that FIG. 1 is a diagram illustrating the overall configuration of the sphygmomanometer 100, FIG. 2 is a function block diagram illustrating the configuration of the sphygmomanometer 100, and FIG. 3 is a flowchart illustrating the flow of a blood pressure measurement process performed by the sphygmomanometer 100.

As seen in FIG. 1, the sphygmomanometer 100 includes a main unit 110 and a sphygmomanometer cuff 150. The sphygmomanometer 100 is an upper arm sphygmomanometer in which the sphygmomanometer cuff 150 is worn on the upper arm of a measurement subject.

The main unit 110 and the sphygmomanometer cuff 150 are provided as independent units, and the main unit 110 is placed on a placement surface of a desk or the like when a blood pressure measurement is to be taken. The main unit 110 and the sphygmomanometer cuff 150 are connected by a connection tube 140 that is connected to an air connection port 146 provided in the sphygmomanometer cuff 150.

A display unit 122 and an operating unit 124 are provided in the main unit 110. The display unit 122 displays blood pressure value measurement results, pulse frequency measurement results, and so on in a visual manner, using numerical values, graphs, or the like. A liquid-crystal panel, for example, is used as the display unit 122. The operating unit 124 is provided with a various types of buttons, such as a power button, a measurement start button, input buttons for inputting information regarding a user of the sphygmomanometer cuff 150, and so on.

The sphygmomanometer cuff 150 has a band shape when viewed from the exterior, and is wrapped around the upper arm of the measurement subject. The sphygmomanometer cuff 150 includes an fluid bladder 161 for applying pressure to the upper arm and a bladder-shaped cover member 166 for wrapping around and affixing the fluid bladder 161 to the upper arm. The fluid bladder 161 is housed within a space provided inside the bladder-shaped cover member 166.

FIG. 2 is a function block diagram illustrating the configuration of the sphygmomanometer shown in FIG. 1. As seen in FIGS. 1 and 2, blood pressure measurement air system components 131 for supplying/exhausting air to/from the fluid bladder 161 housed within the sphygmomanometer cuff 150 are provided inside the main unit 110.

The pressure measurement air system components 131 include a pressure sensor 132 that serves as a pressure detection unit for detecting a pressure in the fluid bladder 161, and a pump 134 and a valve 135 that serve as an inflation/deflation mechanism 133 for inflating/deflating the fluid bladder 161. An oscillation circuit 136, a pump driving circuit 137, and a valve driving circuit 138 for the pressure measurement air system components 131 are provided in the main unit 110.

The main unit 110 is provided with: a central processing unit (CPU) 121 for centrally controlling and monitoring the various constituent elements; a memory unit 123 for storing various types of information such as programs that cause the CPU 121 to carry out predetermined operations, measured blood pressure values, and so on; the display unit 122 for displaying various types of information include blood pressure measurement results; and the operating unit 124 manipulated in order to input various instructions for taking measurements. The CPU 121 also functions as a blood pressure value calculation unit for calculating blood pressure values.

The pressure sensor 132 detects a pressure within the fluid bladder 161 (called a "cuff pressure" hereinafter) and outputs a signal based on the detected pressure to the oscillation circuit 136. The pump 134 supplies air to the fluid bladder 161. The valve 135 opens and closes when maintaining the pressure within the fluid bladder 161, exhausting the air from within the fluid bladder 161, and so on. The oscillation circuit 136 outputs a signal having an oscillation frequency based on an output value from the pressure sensor 132 to the CPU 121. The pump driving circuit 137 controls the driving of the pump 134 based on a control signal supplied from the CPU 121. The valve driving circuit 138 controls the opening/closing of the valve 135 based on a control signal supplied from the CPU 121.

Next, the flow of a blood pressure measurement process performed by the sphygmomanometer 100 will be described with reference to FIG. 3. A program according to this flowchart is stored in advance in the memory unit 123 shown in FIG. 2, and the blood pressure measurement process is carried out by the CPU 121 reading out the program from the memory unit 123 and executing the program.

As shown in FIGS. 2 and 3, when the measurement subject manipulates the operating unit 124 of the sphygmomanometer 100 and turns the power thereto on, the sphygmomanometer 100 is initialized (step S1). Next, when sphygmomanometer 100 enters a state in which measurement can be carried out, the CPU 121 begins driving the pump 134, gradually raising the cuff pressure in the fluid bladder 161 (step S2). When, during the gradual increase of the cuff pressure, the cuff pressure reaches a predetermined required for taking a blood pressure measurement, the CPU 121 stops the pump 134, gradually opens the valve 135 that was closed and gradually exhausts the air from within the fluid bladder 161, thus gradually reducing the cuff pressure (step S3); the cuff pressure is detected while the cuff pressure is being reduced at an extremely slow speed.

Next, the CPU 121 calculates a systolic blood pressure value (a maximum blood pressure value) and a diastolic blood pressure value (a minimum blood pressure value) through a known procedure (step S4). Specifically, while the cuff pressure is gradually decreasing, the CPU 121 extracts sphygmogram information based on an oscillation frequency obtained from the oscillation circuit 136. A blood pressure value is calculated from the extracted sphygmogram information. After the blood pressure value has been calculated in step S4, the calculated blood pressure value is displayed in the display unit 122 (step S5).

Although the measurement method described thus far is based on what is known as a "deflation measurement method", in which the blood pressure value is calculated by detecting a sphygmogram while the fluid bladder is deflating, note that is it of course possible to employ what is known as an "inflation measurement method" in which the blood pressure value is calculated by detecting the sphygmogram while the fluid bladder is inflating.

Structure of Sphygmomanometer Cuff 150

Figure 4:
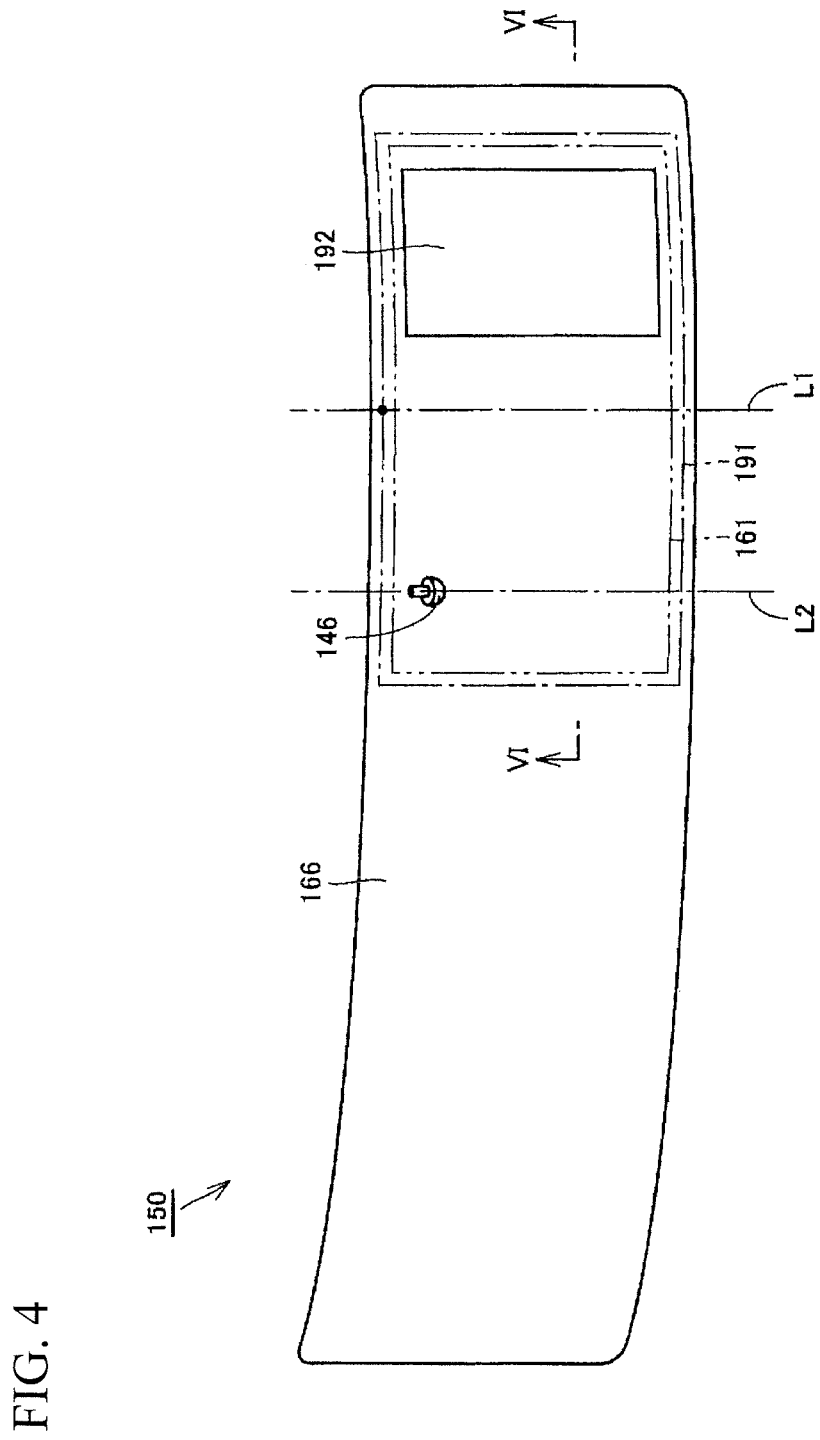
FIG. 4 is a plan view illustrating an unrolled cuff according to the embodiment.
Figure 5:
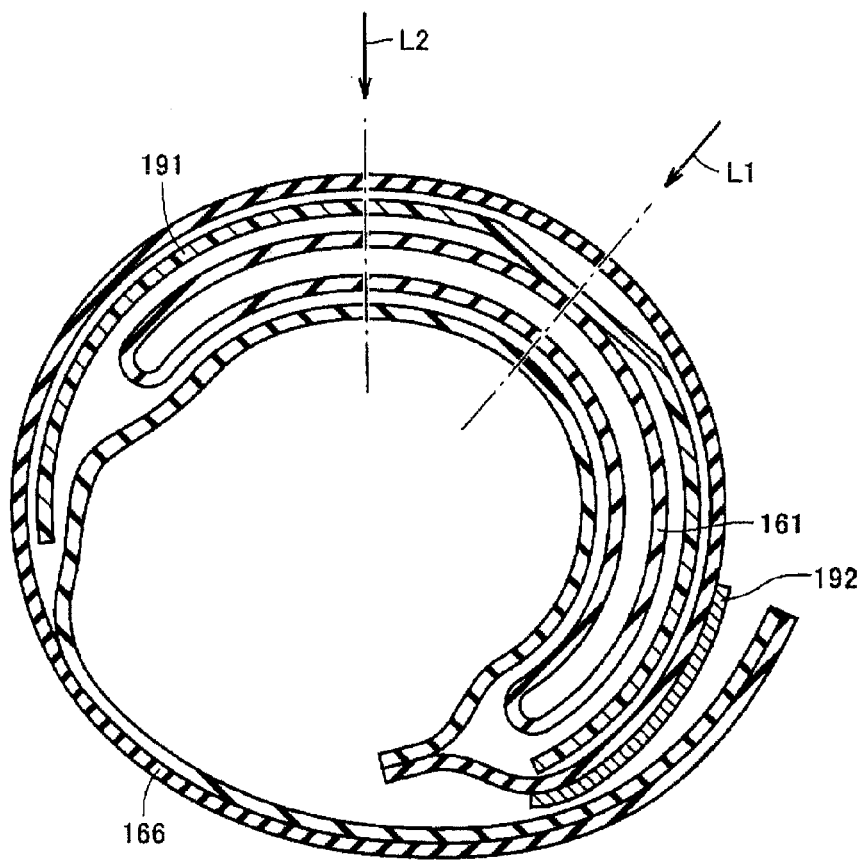
FIG. 5 is a cross-sectional view illustrating a state in which the cuff according to the embodiment has been wrapped around an upper arm.
Figure 6:
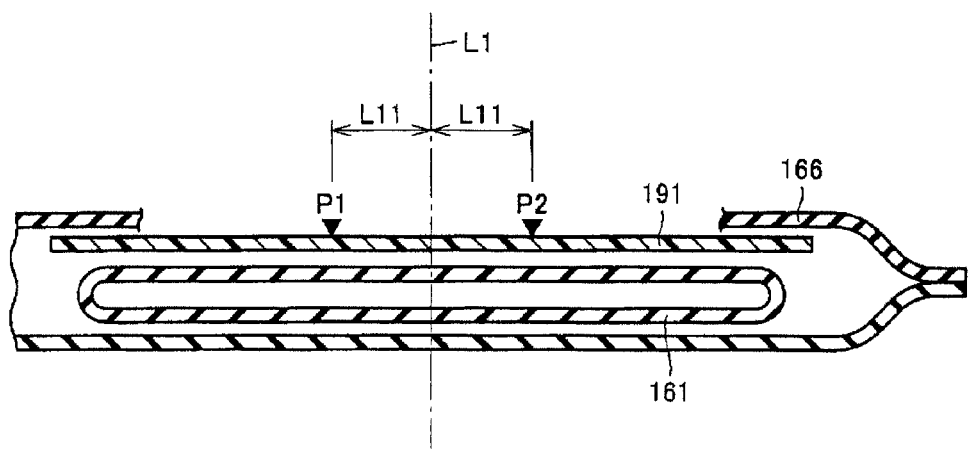
FIG. 6 is a cross-sectional view taken along the VI-VI line in FIG. 4.

Next, the structure of the sphygmomanometer cuff 150 will be described with reference to FIGS. 4 through 6. Note that FIG. 4 illustrates an unrolled state, FIG. 5 is a cross-sectional view illustrating the cuff being wrapped around the upper arm, and FIG. 6 is a cross-sectional view taken along the VI-VI line shown in FIG. 4.

The sphygmomanometer cuff 150 includes: the fluid bladder 161 for applying pressure to the upper arm of the measurement subject; a curler 191 for biasing the fluid bladder 161 toward the upper arm; and the bladder-shaped cover member 166, which is configured as a band and is wrapped around the upper arm of the measurement subject in order to affix the fluid bladder 161 to the upper arm of the measurement subject while housing the fluid bladder 161 and the curler 191.

A surface fastener 192 for affixing one end of the bladder-shaped cover member 166 to the other end of the bladder-shaped cover member 166 when the bladder-shaped cover member 166 is wrapped around the upper arm of the measurement subject is provided on the outer surface of the bladder-shaped cover member 166 in which the fluid bladder 161 is housed. It is preferable for the bladder-shaped cover member 166 to be formed of a material including synthetic fibers such as polyamide (PA), polyester, or the like.

The curler 191 is a curved elastic member for biasing the fluid bladder 161 toward the upper arm. The curler 191 has a band shape when unrolled. The curler 191 is formed in a circular shape extending in the axial direction of the upper arm so as to fit the upper arm, and is a flexible member configured so as to be capable of elastic deformation in the radial direction when wrapped into a ring shape. The curler 191 is formed of a resin member such as polypropylene (PP) in order to achieve a sufficient elastic force.

A material that is highly stretchable is used as the material for the resin sheet of which the fluid bladder 161 is formed; ethylene-vinyl acetate (EVA), polyvinyl chloride (PVC), polyurethane (PU), polyamide (PA), crude rubber, or the like can be given as examples of preferable materials for the resin sheet.

The air connection port 146 is provided in the sphygmomanometer cuff 150 for injecting/exhausting air into/from the fluid bladder 161 from the main unit 110. This air connection port 146 is described in the operating manual of the sphygmomanometer as well as indicated on the sphygmomanometer cuff 150 itself so as to be placed in a top position (L2) of the upper arm when the sphygmomanometer cuff 150 is wrapped around the upper arm. Meanwhile, an artery position (L1) is also indicated on the sphygmomanometer cuff 150.

As seen in FIGS. 5 and 6, it is very important to align the center position of the fluid bladder 161 immediately above the artery when measuring blood pressure, and thus the fluid bladder 161 is held within the bladder-shaped cover member 166 so that the artery position (L1) overlaps with the center position of the fluid bladder 161 that follows the direction in which it is wrapped around the upper arm. The space between the air connection port 146 (the top position (L2)) and the artery position (L1) is set to approximately 40 mm.

Detailed Configuration of Curler 191

Figure 7:
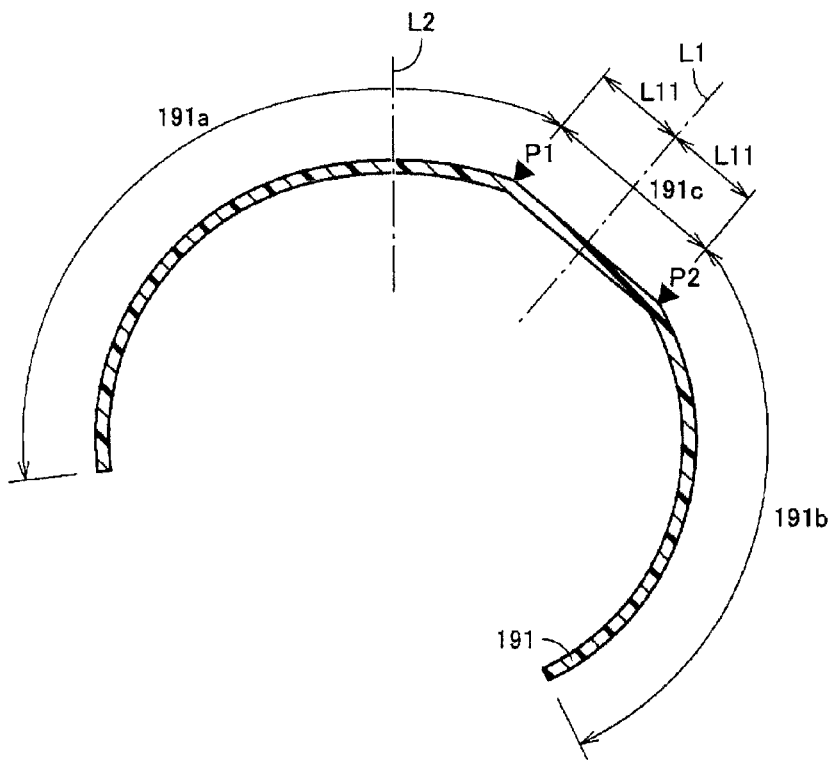
FIG. 7 is a cross-sectional view taken along the VII-VII in FIG. 8, illustrating a state in which a curler employed in the cuff according to the embodiment has been wrapped around the upper arm.
Figure 8:
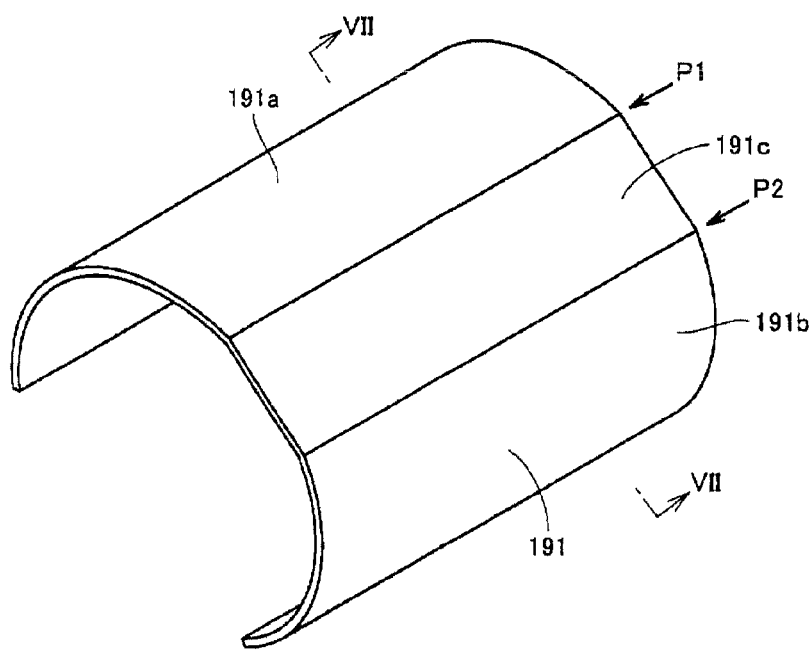
FIG. 8 is a perspective view illustrating a state in which the curler employed in the cuff according to the embodiment has been wrapped around the upper arm.
Figure 9:
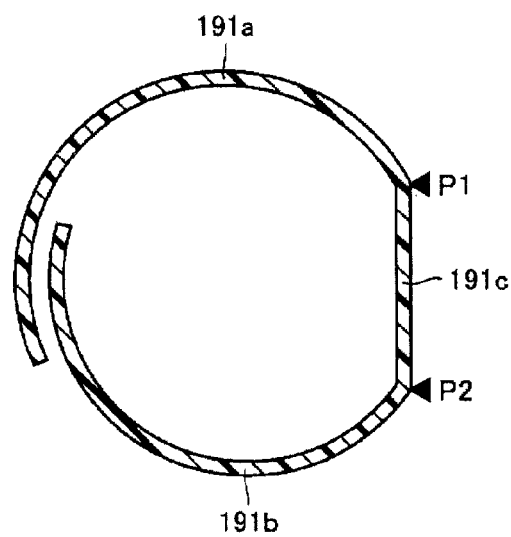
FIG. 9 is a cross-sectional view illustrating a state in which an external force is not applied to the curler employed in the cuff according to the embodiment.

Next, the configuration of the curler 191 according to the present embodiment will be described in detail with reference to FIGS. 7 through 9. FIG. 7 is a cross-sectional view illustrating a state in which the curler 191 is wrapped around the upper arm taken along the VII-VII shown in FIG. 8; FIG. 8 is a perspective view illustrating a state in which the curler 191 is wrapped around the upper arm, and FIG. 9 is a cross-sectional view of the curler 191.

As described above, the curler 191 is formed in a circular shape extending in the axial direction of the upper arm so as to fit the upper arm, and is a flexible member configured so as to be capable of elastic deformation in the radial direction when wrapped into a ring shape. The curler 191 is broadly divided into three regions, or a first curved portion 191a, a second curved portion 191b, and a connection portion 191c that connects the first curved portion 191a and the second curved portion 191b. Note that the first curved portion 191a is formed having a single curvature radius or multiple curvature radii. The same applies to the second curved portion 191b as well.

The point of connection between the first curved portion 191a and the connection portion 191c configures a first flexion point P1 where the curvature radius changes, whereas the point of connection between the second curved portion 191b and the connection portion 191c configures a second flexion point P2 where the curvature radius changes. It is preferable for the connection portion 191c between the first flexion point P1 and the second flexion point P2 to be formed inside of a curve formed by the first curved portion 191a of the curler 191 if that curve was extended from its end at first flexion point P1 and to be formed inside of a curve formed by the second curved portion 191b of the curler 191 if that curve was extended from its end at the second flexion point P2; in the configuration shown in FIG. 7, the connection portion 191c is formed so as to follow a straight line between the first flexion point P1 and the second flexion point P2. Meanwhile, the connection portion 191c is formed so as to span from one end to the other end of the curler 191 in the axial direction thereof.

The distance between the first flexion point P1 and the second flexion point P2 (that is, the length of the connection portion 191c) is approximately 20 mm to approximately 60 mm, and is preferably approximately 20 mm to approximately 40 mm; in the present embodiment, 30 mm (L11=15 mm) is used.

Note that the state illustrated in FIGS. 5 and 7 is a state in which the cuff is affixed to the upper arm, and thus the first curved portion 191a and the second curved portion 191b appear spread out. However, when no external force is acting on the curler 191, the first curved portion 191a and the second curved portion 191b bend inward and partially overlap, as shown in FIG. 9.

Actions and Effects

According to the sphygmomanometer cuff 150 that employs the curler 191 according to the present embodiment, and the sphygmomanometer 100 provided therewith, the first flexion point P1 and the second flexion point P2, where the curvature radius changes, are provided in the curler 191; the straight line-shaped connection portion 191c is provided between the first flexion point P1 and the second flexion point P2 so as to be located inside a curve formed by extending the first curved portion 191a and the second curved portion 191b of the curler 191, according to their respective curvatures, from the respective ends at the first flexion point P1 and the second flexion point P2.

As a result, the center position L1 of the straight line-shaped connection portion 191c is located immediately above the artery position L1 even in the case where the sphygmomanometer cuff 150 is loosely affixed to the upper arm, and thus the distance between the curler 191 and the surface of the upper arm can be reduced more than in the conventional configuration. Accordingly, the direction in which the fluid bladder 161 expands can be aligned with the center direction of the axis of the upper arm. Furthermore, because the fluid bladder 161 is pressurized between the two flexion points, the fluid bladder 161 can be suppressed from wrinkling.

Accordingly, the distance between the curler 191 and the surface of the upper arm is shorter than in the conventional configuration, and thus when taking a blood pressure measurement using the sphygmomanometer, error in the volume change of the fluid bladder 161 can be reduced, which in turn makes it possible to reduce errors in the blood pressure measurement.

Figure 10:
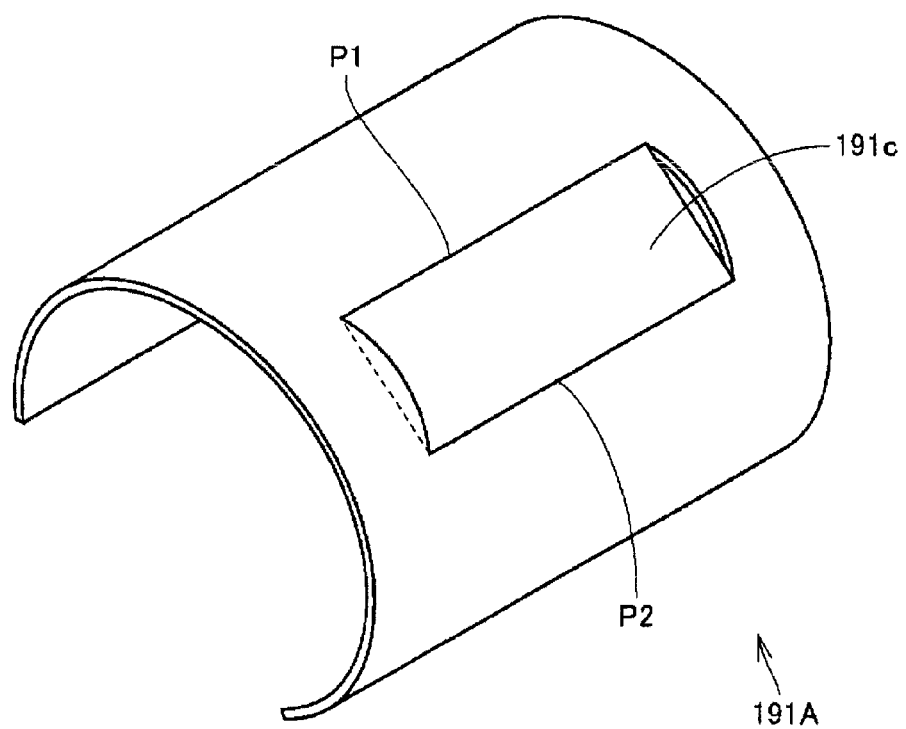
FIG. 10 is a perspective view illustrating another example of a curler employed in the cuff according to the embodiment.

Although the above describes a case in which the straight line-shaped connection portion 191c in the sphygmomanometer cuff 150 is formed spanning from one end to the other end of the curler 191 in the axial direction thereof, it should be noted that, as indicated by a curler 191A shown in FIG. 10, the straight line-shaped connection portion 191c may be formed only in a central portion of the curler 191A in the axial direction thereof.

Figure 11:
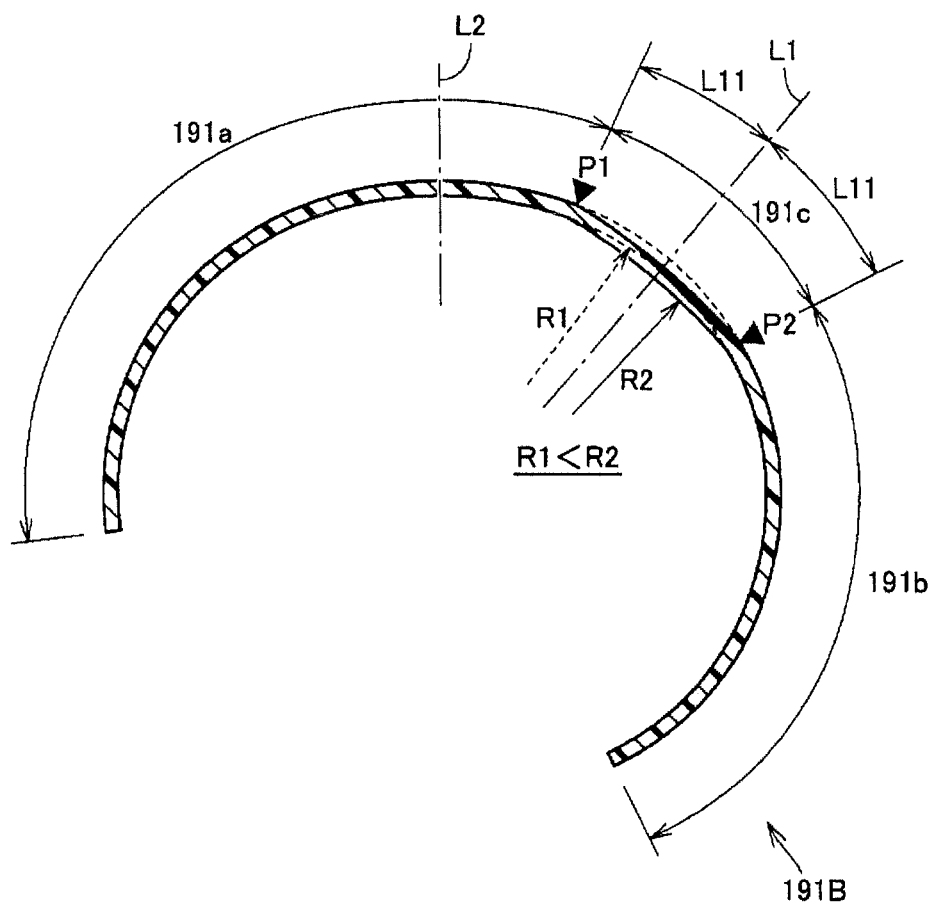
FIG. 11 is a cross-sectional view illustrating yet another example of a curler employed in the cuff according to the embodiment.

It is also possible to employ the configuration of a curler 191B illustrated in FIG. 11, as another configuration of the curler 191. Although the curler 191 has a straight line-shaped connection portion 191c located between the first flexion point P1 and the second flexion point P2, in the curler 191B, the connection portion 191c is formed having a curvature radius R2 that is greater than a curvature radius R1 extending from the first curved portion 191a and the second curved portion 191b, so that the connection portion 191c is located inside a curve formed by extending the first curved portion 191a and the second curved portion 191b of the curler 191 from their ends at the first flexion point P1 and the second flexion point P2, according to the respective curvatures.

Figure 12:
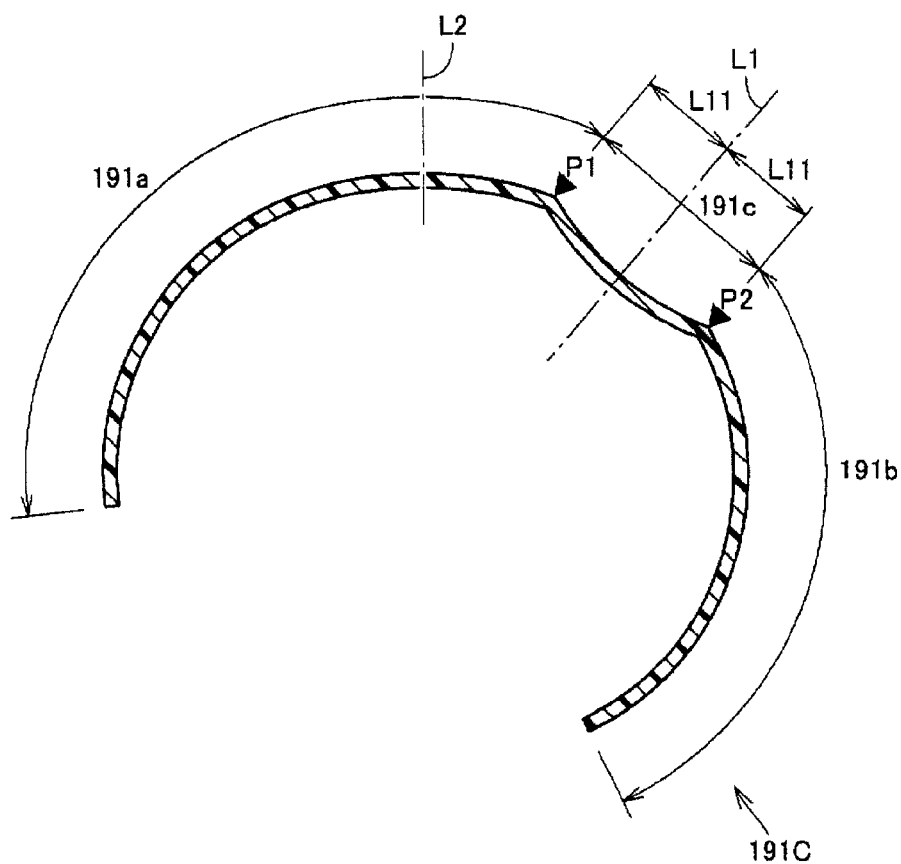
FIG. 12 is a cross-sectional view illustrating yet another example of a curler employed in the cuff according to the embodiment.
Figure 13:
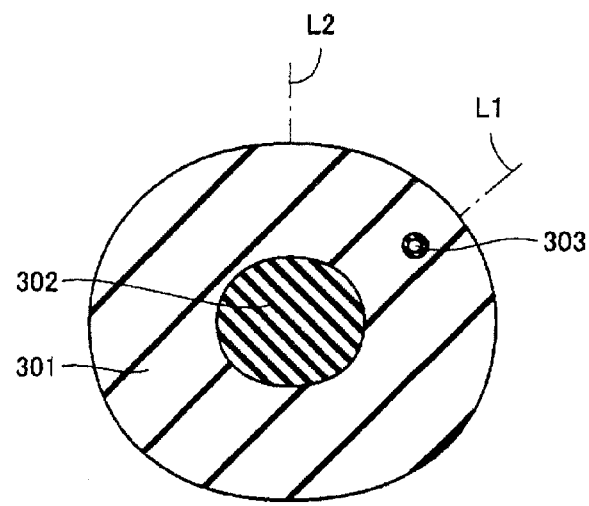
FIG. 13 is a schematic diagram illustrating a cross-section of an upper arm.
Figure 14:
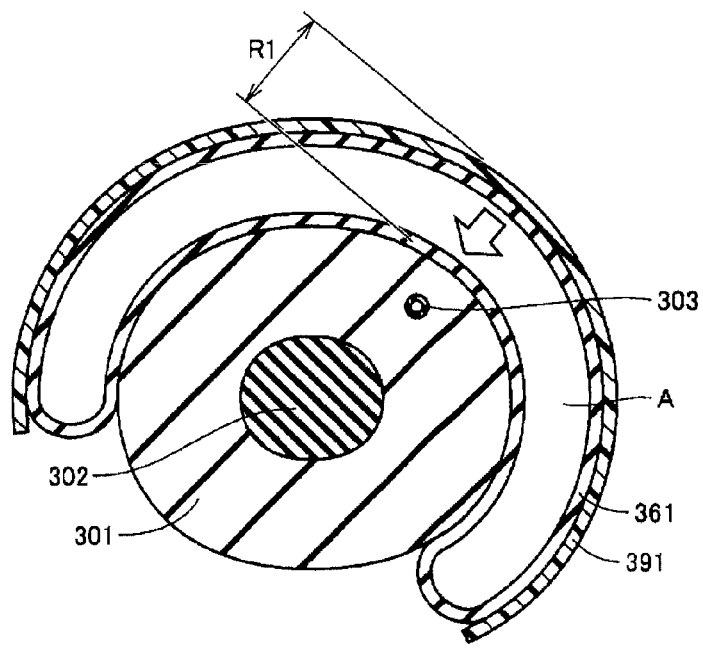
FIG. 14 is a cross-sectional schematic diagram illustrating a state in which a cuff has been properly affixed to the upper arm.
Figure 15:
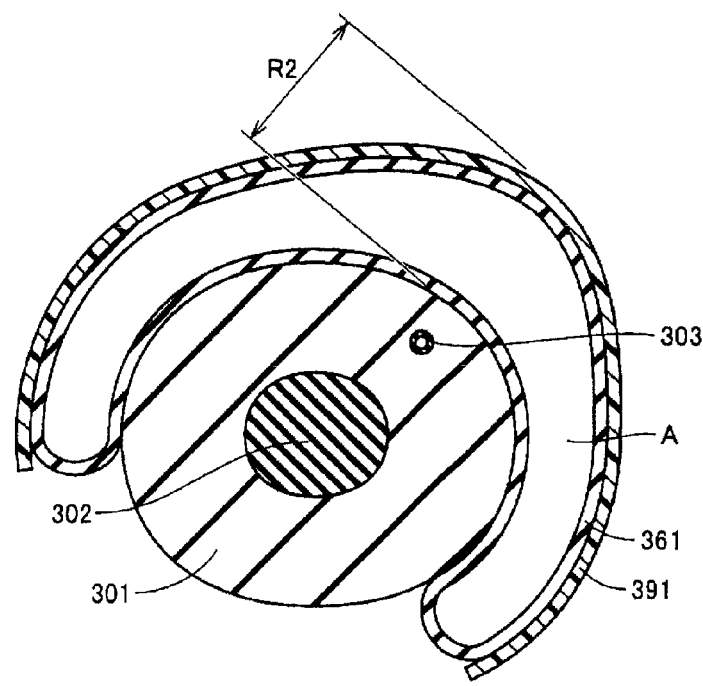
FIG. 15 is a cross-sectional schematic diagram illustrating a state in which a cuff has been wrapped around an upper arm loosely.

It is also possible to employ the configuration of a curler 191C illustrated in FIG. 12, as yet another configuration of the curler 191. In the curler 191C, the connection portion 191c is formed so as to be recessed toward the inner side.

According to the configurations of the stated curler 191B and curler 191C, the distance between the curler 191 and the surface of the upper arm can be reduced more than with the conventional configuration, even in the case where the sphygmomanometer cuff 150 has been loosely affixed to the upper arm. As a result, when taking a blood pressure measurement using the sphygmomanometer, error in the volume change of the fluid bladder 161 can be reduced, which in turn makes it possible to reduce errors in the blood pressure measurement, even in the case where the sphygmomanometer cuff 150 has been loosely affixed.

Meanwhile, although the aforementioned embodiment describes a preferred example in which the sphygmomanometer cuff 150 is provided so that the center position L1 between the first flexion point P1 and the second flexion point P2 overlap with the center position L1 of the fluid bladder 161 that follows the direction in which it is wrapped around the upper arm, according to another embodiment, the distance between the curler 191 and the surface of the upper arm can be reduced more than in the conventional configuration by disposing the connection portion 191c located between the first flexion point P1 and the second flexion point P2 so as to overlap with the center position of the fluid bladder 161.

As a result, when taking a blood pressure measurement using the sphygmomanometer, error in the volume change of the fluid bladder 161 can be reduced, which in turn makes it possible to reduce errors in the blood pressure measurement.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A blood pressure information measurement device cuff comprising:
   a fluid bladder for applying pressure to a measurement area;
   a curler for biasing the fluid bladder toward the measurement area; and
   a bladder-shaped cover member that houses the fluid bladder and the curler and is configured as a band that is wrapped around the measurement area in order to affix the fluid bladder and the curler to the measurement area,
   wherein the curler is formed in a curved shape that follows the direction in which the curler is wrapped around the measurement area, and includes a first flexion point and a second flexion point at which the curvature radius of the curler changes,
   wherein an area between the first flexion point and the second flexion point is formed so as to be further inside from a curve formed by extending the curvature of the curler from the ends of the curler at the first flexion point and the second flexion point, and
   wherein a center position between the first flexion point and the second flexion point overlaps with a center position of the fluid bladder that follows the direction in which the fluid bladder is wrapped around the measurement area,
   wherein a distance between the first flexion point and the second flexion point is approximately 20 mm to approximately 40 mm, and
   wherein the area between the first flexion point and the second flexion point comprises an inner surface of the curler that forms a straight line.

2. A blood pressure information measurement device comprising:
   a blood pressure information measurement device cuff including a fluid bladder for applying pressure to a measurement area, a curler for biasing the fluid bladder toward the measurement area, and a bladder-shaped cover member that houses the fluid bladder and the curler and is configured as a band that is wrapped around the measurement area in order to affix the fluid bladder and the curler to the measurement area;
   an inflation/deflation mechanism that inflates/deflates the fluid bladder; and
   a blood pressure information obtainment unit that obtains blood pressure information,
   wherein the curler is formed in a curved shape that follows the direction in which the curler is wrapped around the measurement area, and includes a first flexion point and a second flexion point at which the curvature radius of the curler changes,
   wherein an area between the first flexion point and the second flexion point is formed so as to be further inside from a curve formed by extending the curvature of the curler from the ends of curler at the first flexion point and the second flexion point,
   wherein a center position between the first flexion point and the second flexion point overlaps with a center position of the fluid bladder that follows the direction in which the fluid bladder is wrapped around the measurement area,
   wherein a distance between the first flexion point and the second flexion point is approximately 20 mm to approximately 40 mm, and
   wherein the area between the first flexion point and the second flexion point comprises an inner surface of the curler that forms a straight line.

3. A blood pressure information measurement device cuff comprising:
   a fluid bladder for applying pressure to a measurement area;
   a curler for biasing the fluid bladder toward the measurement area; and
   a bladder-shaped cover member that houses the fluid bladder and the curler and is configured as a band that is wrapped around the measurement area in order to affix the fluid bladder and the curler to the measurement area,
   wherein the curler is formed in a curved shape that follows the direction in which the curler is wrapped around the measurement area, and includes a first flexion point and a second flexion point at which the curvature radius of the curler changes,
   wherein an area between the first flexion point and the second flexion point is formed so as to be further inside from a curve formed by extending the curvature of the curler from the ends of the curler at the first flexion point and the second flexion point, wherein a portion of the curler between the first flexion point and the second flexion point is disposed so as to overlap with a center position of the fluid bladder, wherein a distance between the first flexion point and the second flexion point is approximately 20 mm to approximately 40 mm, and wherein the area between the first flexion point and the second flexion point comprises an inner surface of the curler that forms a straight line.

4. A blood pressure information measurement device comprising:
   a blood pressure information measurement device cuff including a fluid bladder for applying pressure to a measurement area, a curler for biasing the fluid bladder toward the measurement area, and a bladder-shaped cover member that houses the fluid bladder and the curler and is configured as a band that is wrapped around the measurement area in order to affix the fluid bladder and the curler to the measurement area;
   an inflation/deflation mechanism that inflates/deflates the fluid bladder; and
   a blood pressure information obtainment unit that obtains blood pressure information, wherein the curler is formed in a curved shape that follows the direction in which the curler is wrapped around the measurement area, and includes a first flexion point and a second flexion point at which the curvature radius of the curler changes, wherein an area between the first flexion point and the second flexion point is formed so as to be further inside from a curve formed by extending the curvature of the curler from the ends of the curler at the first flexion point and the second flexion point, wherein a portion of the curler between the first flexion point and the second flexion point is disposed so as to overlap with a center position of the fluid bladder, wherein a distance between the first flexion point and the second flexion point is approximately 20 mm to approximately 40 mm, and wherein the area between the first flexion point and the second flexion point comprises an inner surface of the curler that forms a straight line.

* * * * *